(12) United States Patent
Størup et al.

(10) Patent No.: US 12,036,137 B2
(45) Date of Patent: *Jul. 16, 2024

(54) PROSTHETIC INTERFACE

(71) Applicant: Ossur Iceland ehf, Reykjavik (IS)

(72) Inventors: Martin Lund Størup, Reykjavik (IS); Rowan Cain, Reykjavik (IS); Linda Ros Birgisdottir, Reykjavik (IS); Hogna Hringsdottir, Reykjavik (IS); Sigurdur Asgeirsson, Foothill Ranch, CA (US); Stefan Orn Stefansson, Reykjavik (IS); Andri Orrason, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 50 days.

This patent is subject to a terminal disclaimer.

(21) Appl. No.: 17/693,869

(22) Filed: Mar. 14, 2022

(65) Prior Publication Data

US 2022/0192848 A1 Jun. 23, 2022

Related U.S. Application Data

(63) Continuation of application No. 16/433,319, filed on Jun. 6, 2019, now Pat. No. 11,298,249.

(Continued)

(51) Int. Cl.
*A61F 2/78* (2006.01)
*A61F 2/80* (2006.01)
(Continued)

(52) U.S. Cl.
CPC ............. *A61F 2/80* (2013.01); *A61F 2/7812* (2013.01); *A61F 7/10* (2013.01);
(Continued)

(58) Field of Classification Search
CPC ...................... A61F 2/7812; A61F 2002/7818
See application file for complete search history.

(56) References Cited

U.S. PATENT DOCUMENTS

| 708,685 A | 9/1902 | White |
| 4,655,779 A | 4/1987 | Janowiak |

(Continued)

FOREIGN PATENT DOCUMENTS

| CN | 202051853 U | 11/2011 |
| DE | 102010020262 A1 | 11/2011 |

(Continued)

OTHER PUBLICATIONS

International Search Report from PCT Application No. PCT/US2016/048532, Oct. 26, 2016.

(Continued)

*Primary Examiner* — David H Willse
(74) *Attorney, Agent, or Firm* — Workman Nydegger

(57) ABSTRACT

A prosthetic interface includes a body portion having an open proximal end and a closed distal end including a distal cup. The body portion includes a membrane component having a flexible configuration defining an internal flow space extending along a length of the membrane component between an inner side arranged to face a skin surface of a residual limb and an outer side arranged to face away from the skin surface. At least one material coating is selectively applied to the membrane component that interacts with at least one of the membrane component and the distal cup to define at least one breathable region along the inner side that allows fluid flow between the internal flow space and the residual limb, and at least one impermeable region along the outer side that allows for vacuum suspension between the prosthetic interface and a prosthetic socket.

19 Claims, 8 Drawing Sheets

Related U.S. Application Data

(60) Provisional application No. 62/775,435, filed on Dec. 5, 2018, provisional application No. 62/681,794, filed on Jun. 7, 2018.

(51) Int. Cl.
*A61F 7/10* (2006.01)
*A61F 2/50* (2006.01)

(52) U.S. Cl.
CPC ............ *A61F 2002/5056* (2013.01); *A61F 2002/7818* (2013.01); *A61F 2002/785* (2013.01); *A61F 2002/7875* (2013.01); *A61F 2002/802* (2013.01); *A61F 2002/807* (2013.01)

(56) References Cited

U.S. PATENT DOCUMENTS

| | | | |
|---|---|---|---|
| 4,869,250 A | 9/1989 | Bitterly | |
| 5,258,037 A | 11/1993 | Caspers | |
| 5,480,455 A | 1/1996 | Norvell | |
| 5,534,034 A | 7/1996 | Caspers | |
| 5,571,208 A | 11/1996 | Caspers | |
| 5,885,509 A | 3/1999 | Kristinsson | |
| 6,010,528 A | 1/2000 | Augustine et al. | |
| 6,136,039 A | 10/2000 | Kristinsson et al. | |
| 6,485,776 B2 | 11/2002 | Janusson et al. | |
| 6,626,852 B2 | 9/2003 | Janusson et al. | |
| 6,706,364 B2 | 3/2004 | Janusson et al. | |
| 6,923,834 B2 | 8/2005 | Karason | |
| 6,974,484 B2 | 12/2005 | Caspers | |
| 7,001,563 B2 | 2/2006 | Janusson et al. | |
| 7,105,122 B2 | 9/2006 | Karason | |
| 7,118,602 B2 | 10/2006 | Bjarnason | |
| 7,488,349 B2 | 2/2009 | Einarsson | |
| 7,771,487 B2 | 8/2010 | Mantelmacher | |
| 7,867,286 B2 | 1/2011 | Einarsson | |
| 7,922,775 B2 | 4/2011 | Caspers | |
| 8,034,120 B2 | 10/2011 | Egilsson et al. | |
| 8,052,760 B2 | 11/2011 | Egilsson et al. | |
| 8,097,043 B2 | 1/2012 | Egilsson | |
| 8,114,167 B2 | 2/2012 | Caspers | |
| 8,182,547 B2 | 5/2012 | King | |
| 8,308,815 B2 | 11/2012 | Mccarthy | |
| 8,308,817 B2 | 11/2012 | Egilsson et al. | |
| 8,372,159 B2 | 2/2013 | Mackenzie | |
| 8,382,852 B2 | 2/2013 | Laghi | |
| 8,394,150 B2 | 3/2013 | Laghi | |
| 8,444,703 B2 | 5/2013 | Slemker et al. | |
| 8,475,537 B2 | 7/2013 | King | |
| 8,480,759 B2 | 7/2013 | Pacanowsky et al. | |
| 8,535,389 B2 | 9/2013 | Mckinney | |
| 8,679,194 B2 | 3/2014 | Mackenzie | |
| 8,808,394 B2 | 8/2014 | Laghi | |
| 8,894,719 B2 | 11/2014 | Egilsson et al. | |
| 8,911,506 B2 | 12/2014 | Egilsson et al. | |
| 8,956,422 B2 | 2/2015 | Halldorsson | |
| 8,978,224 B2 | 3/2015 | Hurley et al. | |
| 9,044,348 B2 | 6/2015 | Halldorsson et al. | |
| 9,050,201 B2 | 6/2015 | Egilsson et al. | |
| 9,056,022 B2 | 6/2015 | Egilsson et al. | |
| 9,060,885 B2 | 6/2015 | Egilsson et al. | |
| 9,066,821 B2 | 6/2015 | Egilsson et al. | |
| 9,072,611 B2 | 7/2015 | Mackenzie | |
| 9,072,617 B2 | 7/2015 | Halldorsson et al. | |
| 9,155,636 B1 | 10/2015 | Fikes | |
| 9,168,157 B2 | 10/2015 | Mackenzie | |
| 9,180,027 B2 | 11/2015 | Kettwig et al. | |
| 9,198,780 B2 | 12/2015 | Jonsson et al. | |
| 9,295,567 B2 | 3/2016 | Egilsson et al. | |
| 9,398,963 B2 | 7/2016 | King | |
| 9,468,542 B2 | 10/2016 | Hurley et al. | |
| 9,486,335 B2 | 11/2016 | Halldorsson et al. | |
| 9,615,946 B2 | 4/2017 | Halldorsson et al. | |
| 9,629,732 B2 | 4/2017 | Egilsson et al. | |
| 11,298,249 B2 * | 4/2022 | Størup | A61F 2/7812 |
| 2001/0016781 A1 | 8/2001 | Caspers | |
| 2003/0109908 A1 | 6/2003 | Lachenbruch et al. | |
| 2004/0122528 A1 | 6/2004 | Egilsson | |
| 2005/0149202 A1 | 7/2005 | Schaffer et al. | |
| 2007/0055383 A1 | 3/2007 | King | |
| 2007/0162153 A1 | 7/2007 | Barnes et al. | |
| 2007/0213839 A1 | 9/2007 | Nachbar | |
| 2007/0225824 A1 | 9/2007 | Einarsson | |
| 2008/0221705 A1 | 9/2008 | Scussel | |
| 2010/0125342 A1 | 5/2010 | King | |
| 2010/0185300 A1 | 7/2010 | Mackenzie | |
| 2010/0256780 A1 | 10/2010 | So | |
| 2010/0274364 A1 | 10/2010 | Pacanowsky et al. | |
| 2010/0312360 A1 | 12/2010 | Caspers | |
| 2011/0071649 A1 | 3/2011 | Mckinney | |
| 2011/0092935 A1 | 4/2011 | Hann | |
| 2011/0144769 A1 | 6/2011 | Nakamura | |
| 2011/0282466 A1 | 11/2011 | Laghi | |
| 2012/0191217 A1 | 7/2012 | Mackenzie | |
| 2013/0025315 A1 | 1/2013 | Freeman et al. | |
| 2013/0103125 A1 | 4/2013 | Radspieler et al. | |
| 2014/0025183 A1 | 1/2014 | Kelley et al. | |
| 2014/0249650 A1 | 9/2014 | Aghi et al. | |
| 2014/0277584 A1 | 9/2014 | Hurley et al. | |
| 2014/0277585 A1 | 9/2014 | Kelley et al. | |
| 2014/0289924 A1 | 10/2014 | Cleveland | |
| 2014/0379097 A1 | 12/2014 | Hurley et al. | |
| 2015/0079014 A1 | 3/2015 | Ingvarsson et al. | |
| 2015/0142133 A1 | 5/2015 | Egilsson et al. | |
| 2015/0238330 A1 | 8/2015 | Jonsson | |
| 2015/0359644 A1 | 12/2015 | Sanders et al. | |
| 2016/0022442 A1 | 1/2016 | Kettwig et al. | |
| 2016/0030206 A1 | 2/2016 | Abu Osman et al. | |
| 2016/0081822 A1 | 3/2016 | Zhe et al. | |
| 2016/0143752 A1 | 5/2016 | Hurley et al. | |
| 2016/0199202 A1 | 7/2016 | Jonasson et al. | |
| 2016/0338858 A1 | 11/2016 | Hurley et al. | |
| 2016/0338859 A1 | 11/2016 | Sverrisson et al. | |
| 2016/0346100 A1 | 12/2016 | Sverrisson et al. | |
| 2017/0027719 A1 | 2/2017 | Bache et al. | |
| 2017/0027720 A1 | 2/2017 | Pedtke et al. | |
| 2017/0056212 A1 | 3/2017 | Jonsson et al. | |
| 2017/0105853 A1 | 4/2017 | Jonsson et al. | |
| 2017/0128238 A1 | 5/2017 | Hurley et al. | |
| 2017/0216057 A1 | 8/2017 | Egilsson et al. | |
| 2017/0333223 A1 | 11/2017 | Rasmussen et al. | |
| 2018/0000615 A1 | 1/2018 | Hurley et al. | |
| 2018/0021153 A1 | 1/2018 | Hurley et al. | |
| 2018/0036151 A1 | 2/2018 | Garus et al. | |
| 2018/0046078 A1 | 2/2018 | Karasawa | |
| 2019/0117420 A1 | 4/2019 | Størup | |

FOREIGN PATENT DOCUMENTS

| | | |
|---|---|---|
| EP | 0363654 A2 | 4/1990 |
| EP | 1875881 A1 | 1/2008 |
| EP | 2178481 B1 | 11/2016 |
| EP | 3150120 B1 | 10/2018 |
| JP | 2015058013 A | 3/2015 |
| SU | 829095 A1 | 5/1981 |
| WO | 2012039835 A1 | 3/2012 |
| WO | 2014182767 A1 | 11/2014 |

OTHER PUBLICATIONS

Ossur, "Icecross Seal-In X5: For TT/TF Users, Instructions for Use", www.ossur.com, 2010, 68 Pages.

"Prototype Prosthetic Cooling System Wins UTSA Entrepreneurship Competition", OandP.com, May 3, 2013, 3 Pages. Retrieved from Internet on Apr. 20, 2016, http://www.oandp.com/articles/news_2013-05-03_02.asp.

Bertels et al., "Breathable Liner for Transradial Prostheses," Proceedings of the 2011 MyoElectric Controls/Powered Prosthetics Symposium, Aug. 14, 2011, 3 Pages.

(56) References Cited

OTHER PUBLICATIONS

International Search Report from PCT Application No. PCT/US2019/035730, Sep. 6, 2019.

* cited by examiner

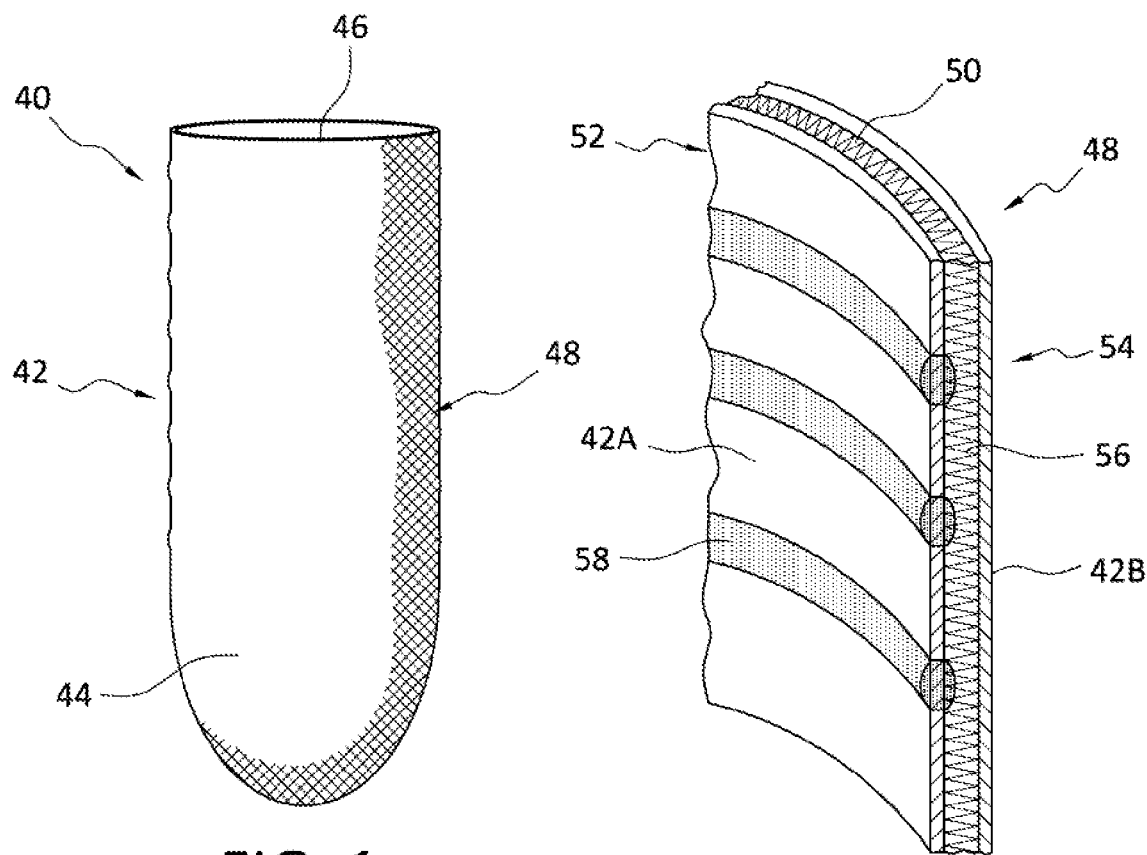
FIG. 1
FIG. 1A
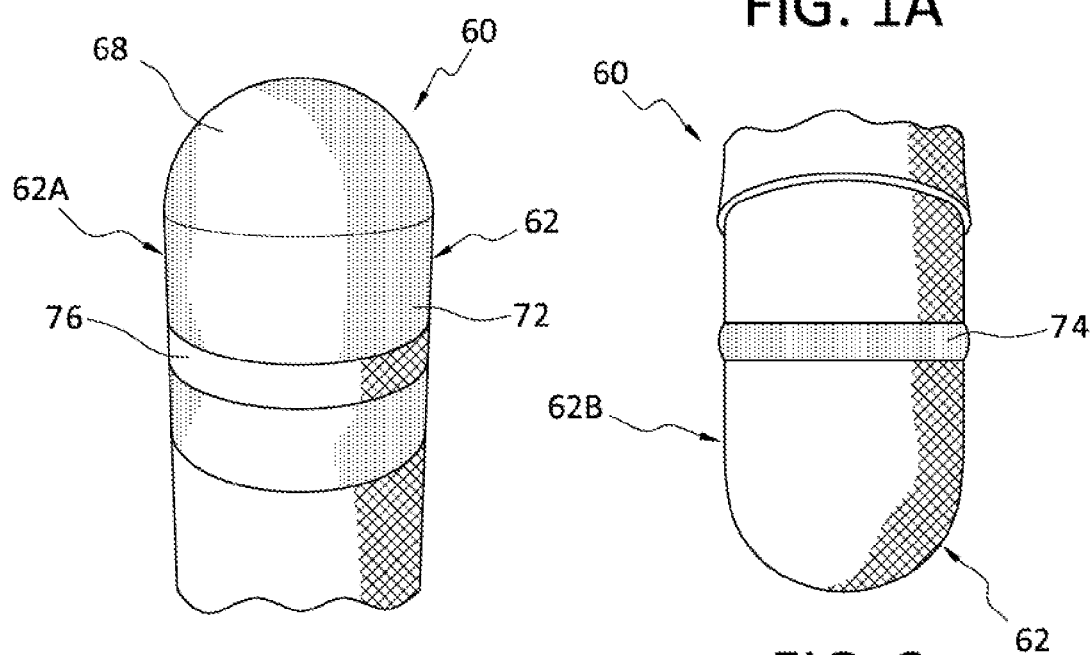
FIG. 2
FIG. 3

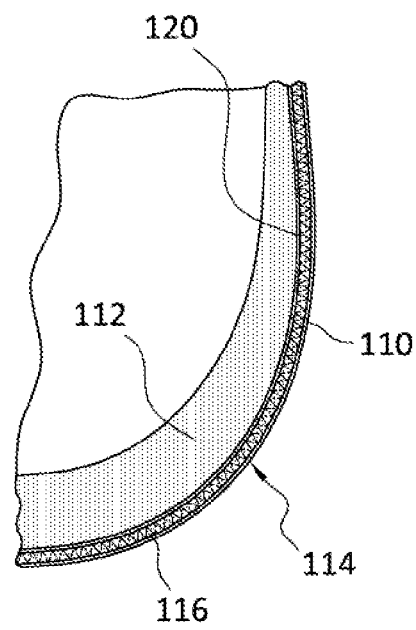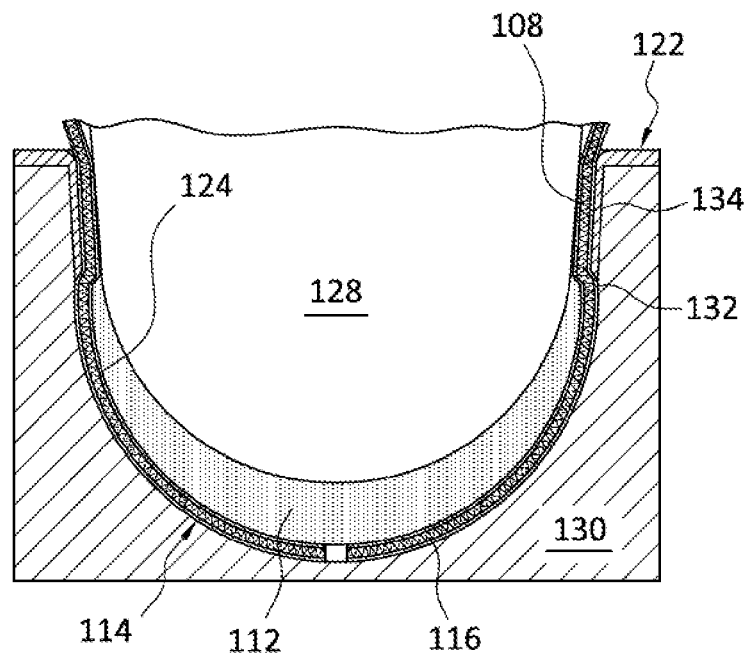
FIG. 7    FIG. 8
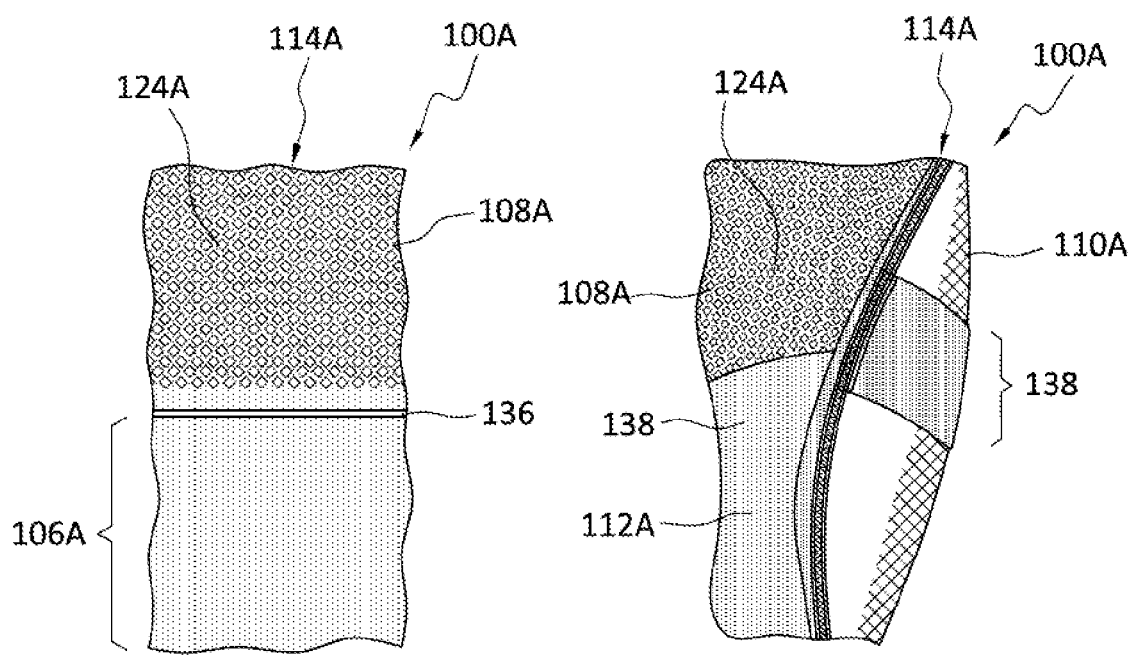
FIG. 9    FIG. 10

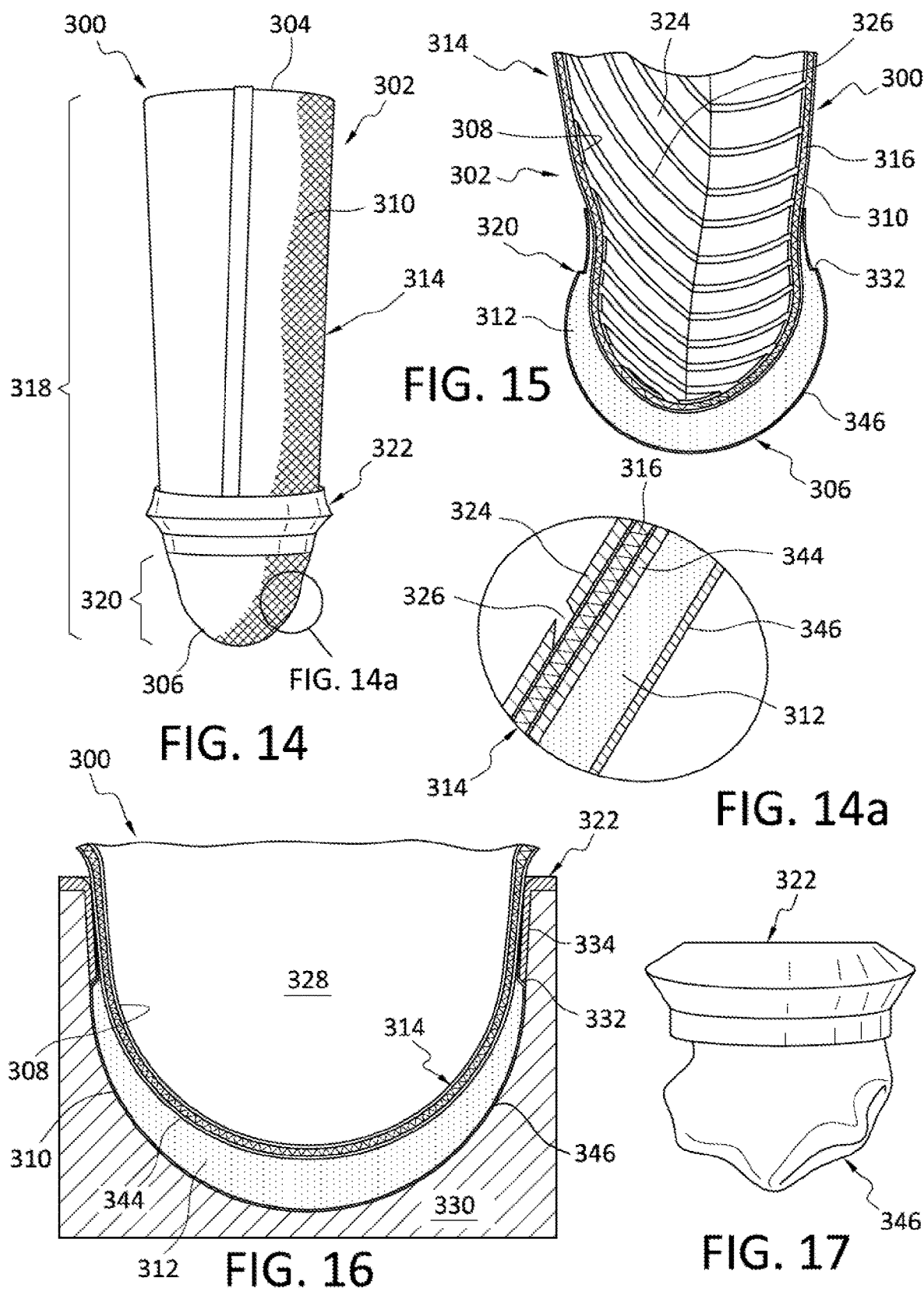

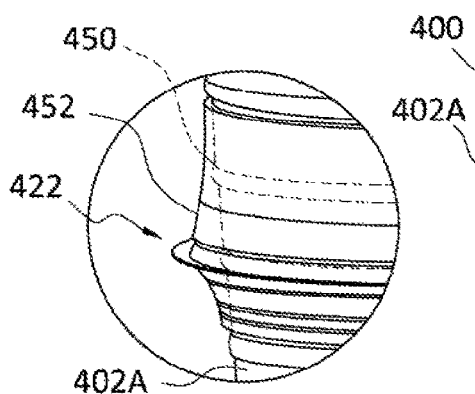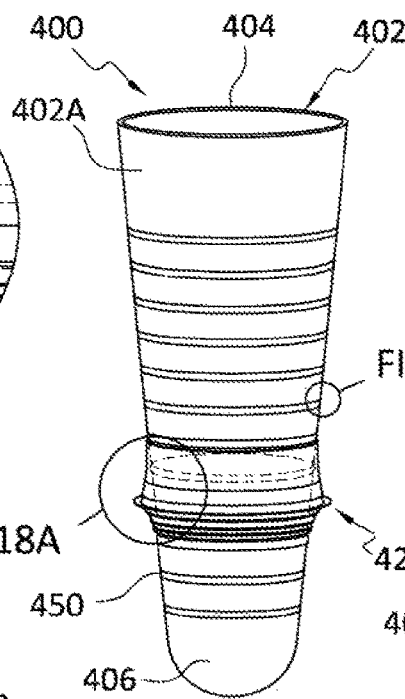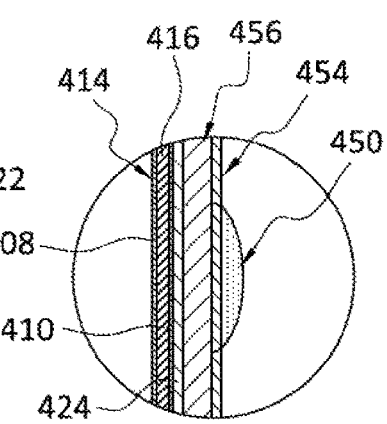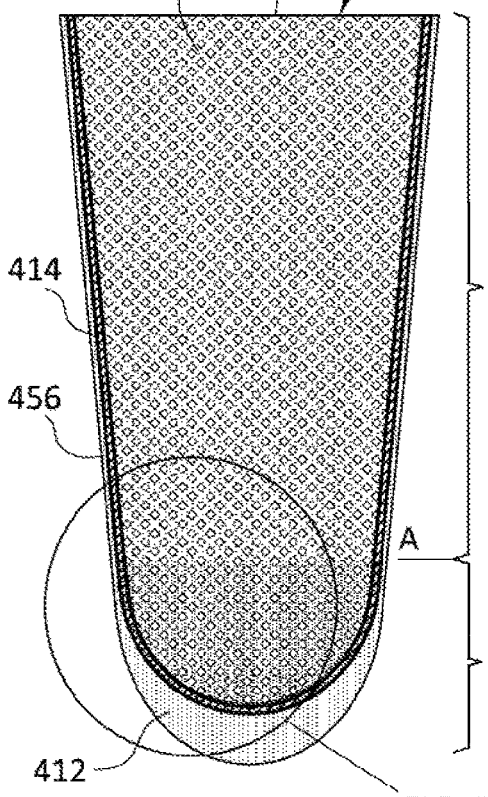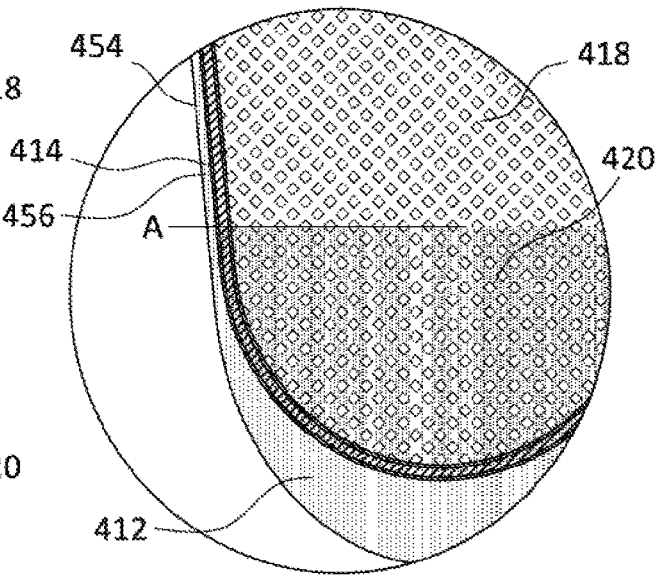

PROSTHETIC INTERFACE

TECHNICAL FIELD

The disclosure relates to a prosthetic interface including a membrane component for use in a prosthetic system.

BACKGROUND

Prosthetic liners are widely used as an interface between a residual limb and a socket that attaches to the residual limb. Prosthetic liners provide padding or pressure distribution that create greater comfort for a user and contribute to the suspension of the socket on the residual limb or what keeps the prosthetic socket attached to the residual limb. Prosthetic liners made of solid elastomers like silicone, copolymer gel, or polyurethane have been commercially available and used for many years as the medium next to the skin in the majority of lower extremity prostheses.

One method of suspension is vacuum suspension where the socket seals airtight against the prosthetic liner and air present in the space between the prosthetic liner and the socket is pulled or forced out. This creates a suction tending to retain the residual limb within the socket, reduce pistoning, and improve stability. Disadvantageously, however, vacuum suspension can only be used with sockets and prosthetic liners that are airtight, which tends to result in heat and perspiration buildup inside of the prosthetic liner.

Because of this buildup of heat and moisture, the skin of the residual limb may become susceptible to sores, allergies, and skin diseases. Problems such as inflammation and infection are also common, particularly if the prosthetic liner and residual limb are not cleaned appropriately or frequently. Perspiration also decreases the friction between the residual limb and the prosthetic liner. This can cause action between the prosthetic liner and the residual limb that macerates the skin, as well as creates the potential for catastrophic failure of the suspension of the residual limb, which can lead to damage and/or injury. Existing prosthetic liners thus struggle with managing the buildup of heat and moisture inside of the prosthetic liner while providing an airtight interface that allows the prosthetic liner to seal against a socket for vacuum suspension.

These problems also exist in other types of prosthetic interfaces such as prosthetic socks, prosthetic sleeves, and other members that create at least part of the interface between the residual limb and the prosthetic socket.

Accordingly, there is a need for a prosthetic liner that more effectively manages heat and moisture and allows for secure vacuum suspension of a residual limb within a socket.

SUMMARY

Embodiments of the present disclosure include a prosthetic interface having a body portion formed at least in part by a membrane component having a flexible configuration defining an internal flow space extending along a length of the membrane component between an inner side arranged to face a skin surface of a residual limb and an outer side arranged to face away from the skin surface. A distal cup is formed of a polymeric material at the distal end of the body portion.

At least one material coating is selectively applied to the membrane component such that it interacts with at least one of the membrane component and the distal cup to provide different features and/or properties to the prosthetic interface. For instance, the at least one material coating can be selectively applied to the membrane component such that it defines at least one breathable region along the inner side of the membrane component that allows fluid flow between the internal flow space and the skin surface, and at least one impermeable region along the outer side that allows for vacuum suspension between the prosthetic interface and a prosthetic socket. These breathable and impermeable regions advantageously help manage the buildup of heat and fluid within the prosthetic interface without compromising the ability of the prosthetic interface to form a reliable vacuum suspension between the prosthetic interface and a corresponding prosthetic socket.

According to a variation, the at least one material coating can comprise a silicone coating defining a plurality voids along the inner side that in the breathable region allow fluid flow between the skin surface and the internal flow space, and in the impermeable region allow the polymeric material forming the distal cup to fill the internal flow space between the inner side and the outer side. This interaction between the at least one material coating and the membrane component and the distal cup advantageously provides a breathable interface for the removal of heat and/or moisture from the residual limb, improving user comfort without compromising the ability of the prosthetic interface to form a seal between the prosthetic liner and the socket for vacuum suspension. The filling of the internal flow space with the polymeric material forming the distal cup also beneficially prevents or reduces the likelihood of the membrane component from collapsing when an elevated vacuum is applied to a distal region of a prosthetic socket.

According to a variation, at least one seal component is attached to the body portion over the impermeable region. When the prosthetic interface is inserted in the socket, the at least one seal component can create an airtight seal with the impermeable region to allow for secure vacuum suspension between the prosthetic interface and the socket.

According to a variation, the at least one coating material can comprise a first material coating applied to the inner side of the membrane component and defining at least one permeable band, and a second material coating applied to the first material coating such that the first material coating is located between the second material coating and the inner side of the membrane component. A portion of the second material coating passes through the at least one permeable band and extends between the inner side and the outer side of the membrane component, which, in turn, forms the impermeable region on the outer side. This allows the at least one seal component to be attached to the impermeable region on the outer side corresponding to the permeable band, allowing for vacuum suspension between the prosthetic interface and the socket. Moreover, the at least one breathable region can include a first breathable region on the inner side, and a second breathable region on the outer side beyond the impermeable region.

According to variation, the at least one breathable region extends along the entire inner side of the membrane component. For example, the membrane component can be permeable to perspiration and positioned inside of a body portion formed of a silicone material. The at least one material coating is selectively applied to the entire outer side of the membrane component. This physically blocks or limits the silicone material forming the body portion from impregnating the internal flow space of the membrane component, maintaining the breathable region along the entirety of the inner side. This can beneficially allow for the entire residual limb to breath inside of the prosthetic interface. In addition, the impermeable region and the breathable region overlap one another along a longitudinal axis of the membrane component.

BRIEF DESCRIPTION OF THE DRAWINGS

These and other features, aspects, and advantages of the present disclosure will become better understood regarding the following description, appended claims, and accompanying drawings.

FIG. 1 is a side view of a prosthetic interface according to an embodiment.

FIG. 1A is a cross section view of the prosthetic interface in FIG. 1 according to an embodiment.

FIG. 2 is a distal inverted view of a prosthetic interface according to another embodiment.

FIG. 3 is a distal view of the prosthetic interface in FIG. 2 with a second material coating applied.

FIG. 7 is a distal cross section view of the prosthetic interface in FIG. 5A.

FIG. 8 is a schematic cross section of a mold assembly for molding the prosthetic interface in FIG. 5A.

FIG. 9 is a detailed view of the inner side of a membrane component according to another embodiment.

FIG. 10 is a detailed cross section view of the inner side of the membrane component in FIG. 9 with a distal cup attached.

FIG. 14 is a side view of a prosthetic interface according to another embodiment.

FIG. 14A is a detailed cross section of the prosthetic interface in FIG. 14.

FIG. 15 is a cross section of the prosthetic interface in FIG. 14.

FIG. 16 is a schematic cross section of a mold assembly for molding the prosthetic interface in FIG. 14.

FIG. 17 is a side view of a seal component according to an embodiment.

FIG. 18 is a side view of a prosthetic interface according to another embodiment.

FIG. 18A is a detailed side view of the prosthetic interface in FIG. 18.

FIG. 18B is a detailed cross section view of the prosthetic interface in FIG. 18.

FIG. 19 is a cross section view of the prosthetic interface in FIG. 18.

FIG. 20 is another detailed cross section view of the prosthetic interface in FIG. 18.

Figure 4A:
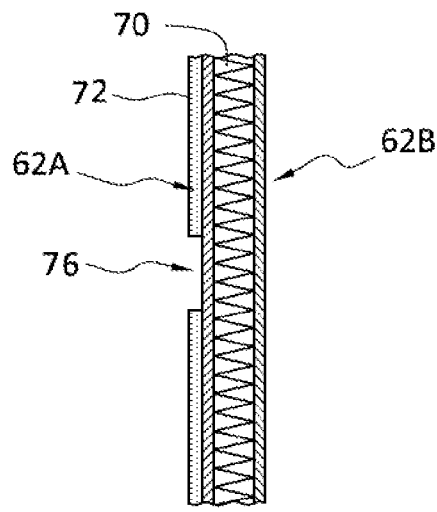
FIG. 4A is a cross section view of the prosthetic interface in FIG. 2.

The drawing figures are not necessarily drawn to scale, but instead are drawn to provide a better understanding of the components, and are not intended to be limiting in scope, but to provide exemplary illustrations. The figures illustrate exemplary configurations of a suspension liner, and in no way limit the structures or configurations of a suspension liner and components according to the disclosure.

DETAILED DESCRIPTION OF VARIOUS EMBODIMENTS

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, that there is no intention to limit the disclosure to the specific embodiments disclosed, but on the contrary, the intention covers all modifications, alternative constructions, combinations, and equivalents falling within the spirit and scope of the disclosure.

For further ease of understanding the embodiments of the present disclosure, a description of a few terms is necessary. As used herein, the term "proximal" has its ordinary meaning and refers to a location that is closer to the heart than another location. Likewise, the term "distal" has its ordinary meaning and refers to a location that is further from the heart than another location.

The terms "rigid," "flexible," and "resilient" may be used herein to distinguish characteristics of portions of certain features of the prosthetic interface. The term "rigid" is intended to denote that an element of the device is generally devoid of flexibility. On the other hand, the term "flexible" is intended to denote that features are capable of repeated bending such that the features may be bent into retained shapes or such that the features do not retain a general shape, but rather continuously deform when force is applied. The term "resilient" is used to qualify such flexible features as generally returning to an initial general shape without permanent deformation. As for the term "semi-rigid," this term is used to connote properties of elements that provide support and are free-standing; however, such elements may have some degree of flexibility or resiliency.

It will be understood that unless a term is expressly defined in this application to possess a described meaning, there is no intent to limit the meaning of such term, either expressly or indirectly, beyond its plain or ordinary meaning.

Any element in a claim that does not explicitly state "means for" performing a specified function, or "step for" performing a specific function is not to be interpreted as a "means" or "step" clause as specified in 35 U.S.C. § 112(f).

FIGS. 1 and 1A illustrate a prosthetic interface 40 according to an embodiment including a body portion 42 having a distal end 44, which is closed, and a proximal end 46, which is open. The prosthetic interface 40 is shown as a prosthetic liner but can be a prosthetic sock, a prosthetic sleeve, or any other suitable prosthetic. The body portion 42 defines an inner side 42A of the prosthetic interface 40 arranged to face the skin of a user, and an outer side 42B of the prosthetic interface 40 arranged to face away from the skin of the user.

The body portion 42 is formed at least in part from a membrane component 48 having a flexible configuration defining the inner side 42A, the outer side 42B, an internal flow space 50 extending along a length of the membrane component 48 between the inner side 42A and the outer side 42B that is capable of transporting fluid through the body portion 42 and relative to the residual limb. For instance, the internal flow space 50 can be capable of transporting heat and/or fluid though the body portion 42 and away from a residual limb. In other embodiments, the internal flow space 50 is capable of transporting fluid to or toward the skin surface of the residual limb. It will be appreciated that the term "fluid" may refer to any liquid or gas, including, but not limited to, air, sweat, water, vapor, or other suitable matter. For instance, the internal flow space 50 can beneficially allow for air to flow through the membrane component 48 along a length of the prosthetic interface 40, which, in turn, can help lower the temperature inside of the prosthetic interface 40 and/or remove moisture from the residual limb. Optionally, a distal cup made of a polymeric material can be attached to a distal portion of the membrane component 48.

In the illustrated embodiment, the membrane component 48 comprises a spacer structure including a first layer 52 adapted to face the skin of the user and a second layer 54 adapted to face away from the skin of the user, between which a plurality of supporting elements 56 are arranged that hold the first layer 52 and the second layer 54 at a distance from each other and connect them.

Between the first layer 52 and the second layer 54, the supporting elements 56 form the internal flow space 50. According to an embodiment, at least part of the first layer 52 is permeable to fluid and/or breathable such that heat, and fluid can move from the residual limb into the internal flow space 50. Air may then ventilate or move through the internal flow space 50 and along a length of the prosthetic interface 40 to at least in part remove the heat and fluid from the membrane component 48, providing temperature and moisture control to the residual limb. This can advantageously lower the temperature of the residual limb and/or remove sweat from the inside of the prosthetic interface 40, improving health of the residual limb and user comfort.

The first layer 52 may define a plurality of holes having the same or different sizes to allow for improved breathability and/or mechanical fixing to a material coating as described below. According to a variation, the supporting elements 56 include wicking threads adapted to wick sweat from the first layer 52 toward the second layer 54 and away from the skin interface. In another embodiment, the first layer 52 can comprise a hydrophobic layer and the supporting elements 56 can include hydrophilic monofilaments arranged to direct sweat away from the skin interface and out through the membrane component 48.

At least one of the first layer 52 and the second layer 54 can be a textile layer. The layers can be made of yarn, polyamide, polyester, wool, cellulosic fiber, elastane, combinations thereof, or any other suitable material. The first layer 52 and/or the second layer 54 can be formed of elastic or elasticized materials. The first layer 52 and/or the second layer 54 can be formed of a foam material. The supporting elements 56 can comprise nanofibers, microfilament yarn, combinations thereof, or another suitable element. The supporting elements 56 are generally oriented differently than the first layer 52 and the second layer 54. For instance, the supporting elements 56 can extend in a generally normal direction between the first layer 52 and the second layer 54, in a generally oblique direction between the first layer 52 and the second layer 54, and/or the supporting elements 56 can intersect one another between the first layer 52 and the second layer 54.

It will be appreciated that while the membrane component 48 is described as a spacer structure, in other embodiments, the structure can comprise a foam material structure, a double layered textile structure, a 3D textile, a technical knitting structure, combinations thereof or any other suitable material structure forming the breathable space.

At least one material coating 58 is applied to the membrane component 48 such that it interacts with at least one of the membrane component 48 and the distal cup. The interaction between the at least one material coating 58 and the membrane component 48 and/or the distal cup provides different features and/or properties to the prosthetic interface 40. For instance, the at least one material coating 58 can be applied to the inner side 42A of the membrane component 48 such that it creates at least one breathable region along the inner side 42A and at least one impermeable region extending to the outer side 42B of the body portion 42. It will be appreciated that as used herein at least one breathable region and at least one impermeable region can comprise, one, two, three, or any suitable number of regions.

In an embodiment, the at least one material coating 58 can be applied to the inner side 42A to provide cushioning and/or to adhere to a skin surface of a residual limb, in order to ensure the orientation of the prosthetic interface 40 with respect to the residual limb. According to another embodiment, the at least one material coating 58 is applied to the outer side 42B of body to promote increased adherence and/or rotation control between the prosthetic interface 40 and a prosthetic socket. The at least one material coating 58 can comprise a frictional material, a polymeric material, silicone, polyurethane, foam, open celled elastomeric foam, a copolymer, combinations thereof, or any other suitable material.

The at least one material coating 58 can be applied in areas set apart from each other on the respective sides of the body portion 42, for example in the shape of rings, strips, dots, hexagons, waves, or in other shapes. In an embodiment, the at least one material coating 58 is applied to the surfaces only in particularly stressed areas of the prosthetic interface 40, whereas less stressed areas are not provided with the coating. This beneficially increases the level of comfort and can improve the exchange of heat and of moisture from the skin through the internal flow space 50 of the membrane component 48 to the environment.

In other embodiments, the at least one material coating 58 can comprise a bar or elongated strip of polymeric material applied to the inner side 42A of the body portion 42 arranged to be worn over a user's tibia. The bar can extend in an axial direction and has a thickness selected to provide added cushioning to the tibia.

In other embodiments, the at least one material coating 58 can be formed as patches, distinct zones, nubs, protuberances, circular protrusions, grids, anatomical patterns, honeycomb patterns, or any other suitable pattern on the membrane component 48. For instance, the at least one material coating 58 can include a first region or projections shaped as waves or squiggles and a second region of projections shaped as linear segments. Both regions can define a width that tapers in a distal direction such that the first region is wider than the second region. The first region can provide enhanced rotational control relative to the second region.

The at least one material coating 58 can be applied over an entire side or surface of the membrane component 48. In an embodiment, the at least one material coating 58 can be moisture-permeable to promote movement of fluid into and/or from the internal flow space 50. Large areas of the at least one material coating 58 likewise can include perforations, pores, or openings to allow air and moisture to pass through. In other embodiments, the at least one material coating 58 can comprise a thin silicone coating that permits air and moisture to pass through.

According to one variation, the at least one material coating 58 can be configured to controllably bleed or wet into the internal flow space 50 of the membrane component 48. This can improve the durability of the at least one material coating 58 by reducing the likelihood of unintended separation of the at least one material coating 58 from the membrane component 48. It can also form one or more impermeable regions on the membrane component 48 that are airtight and capable of forming a seal between the prosthetic interface 40 and a prosthetic socket.

As discussed above, the at least one material coating 58 can be configured to interact with at least one of the membrane component 48 and the distal cup to define discrete breathable and impermeable regions on the body portion 42. These breathable and impermeable regions help mitigate the buildup of fluid and heat within the prosthetic interface 40 without compromising its ability to form a reliable vacuum suspension between the prosthetic interface and a corresponding prosthetic socket. More particularly, the breathable region can define a breathable interface along the inner side of the membrane component 48 to help move fluid and heat relative to the residual limb through the internal flow space. The impermeable region on the outer side of membrane component 48 can be associated with at least one seal component to help maintain a vacuum between the prosthetic interface 40 and the prosthetic socket by preventing atmosphere from entering a space defined distal to the seal component. As such, the prosthetic interface 40 can both breathe and allow for vacuum suspension between the prosthetic interface 40 and the prosthetic socket.

Figure 4B:
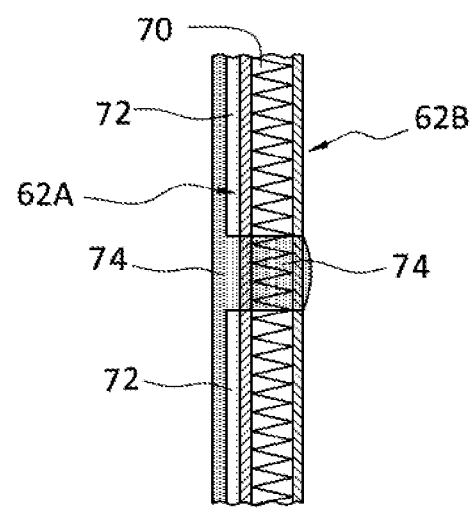
FIG. 4B is a cross section view of the prosthetic interface in FIG. 3.

FIGS. 2-4 show a prosthetic interface 60 according to another embodiment comprising a prosthetic sock having a body portion 62 with a closed distal end and an open proximal end. Referring to FIG. 2, which shows the prosthetic interface 60 in an inverted position for ease of reference, the body portion 62 is formed at least in part by a membrane component 68 having a flexible configuration defining internal flow space 70 (shown in FIGS. 4A and 4B) along a length of the membrane component 68 between an inner side 62A and an outer side 62B of the body portion 62 or the membrane component 68. Like in other embodiments, the internal flow space 70 is capable of transporting heat and/or fluid through the membrane component 68 and relative to a skin surface of a residual limb. For instance, the internal flow space 70 can help transport heat and/or perspiration through the membrane component 68 away from the skin surface of the residual limb. The membrane component 68 is preferably a spacer structure but can comprise a foam material, a double-layered textile, a thick textile, a 3D spacer, a technical knitting, or any other suitable structure.

In the illustrated embodiment, at least one material coating comprising a first material coating 72 and a second material coating 74 are selectively applied to the inner side 62A of the membrane component 68 of the body define discrete breathable and impermeable regions along a length of the body portion 62. The first material coating 72 can be applied first to a selected length of the inner side of the distal end. The first material coating 72 can be impermeable and configured not to bleed or seep into the internal flow space 70, making the corresponding portion of the inner side 62A impermeable or substantially impermeable to fluid. Alternatively, the bleeding of the first material coating 72 into the internal flow space 70 is blocked or limited by a coating layer on the inner side 62A facing the first material coating 72. This can help prevent a distal cup molded onto the membrane component 68 from bleeding into the internal flow space 70 of the membrane component 68 during formation or injection molding of the distal cup on the inner side of the prosthetic interface 60.

As best seen in FIG. 2 and FIG. 4A, the first material coating 72 is applied to the inner side 62A such that the first material coating 72 leaves or defines at least one uncoated or permeable region 76 on the inner side 62A of the membrane component 68. The second material coating 74 is then applied over the first material coating 72 in the area of the permeable region 76. Like the first material coating 72, the second material coating 74 has an impermeable configuration. The second material coating 74 however is configured to bleed through the membrane component 68, including the internal flow space 70.

As seen in FIGS. 3 and 4B, the arrangement of the first material coating 72 and the second material coating 74 protects the internal flow space 70 from the second material coating 74 except in the permeable region 76, which permits the second material coating 74 to completely bleed through the membrane component 68 from the inner side 62A to the outer side 62B in the area of the permeable region 76. This allows the second material coating 74 to physically form an air tight bridge extending between the inner side 62A and the outer side 64B of the membrane component 68 at or near the permeable region 72 as seen in FIG. 4B. This beneficially can allow a seal component or element to be attached to the second material coating 74 on the outer side 62B of the membrane component 68, permitting vacuum suspension of the prosthetic interface 60. As such, the interaction of the first and second material coatings with the membrane component 68 can form a distal region on the body portion 62 that is substantially impermeable to fluid or air tight, and a region proximal to the impermeable region that is breathable. This helps mitigate the buildup of fluid and heat without compromising the ability of the prosthetic interface 60 to form a reliable vacuum suspension.

FIGS. 5-8 shows a prosthetic interface 100 according to yet another embodiment comprising a prosthetic liner including a body portion 102 having a proximal end 104, which is open, and a distal end 106 which is closed. The body portion 102 or membrane component described below defines an inner side 108 arranged to face a user's skin, and an outer side 110 arranged to face away from the user's skin. A distal cup is located at the distal end 106 and provides cushioning and distribution of pressure at the distal end of the residual limb, enhancing user comfort and compliance. The distal cup 112 can be formed of a polymeric material such as silicone.

The body portion 102 is formed at least in part by a membrane component 114 having a flexible configuration defining an internal flow space 116 extending along a length of the membrane component 114 between the inner side 108 and the outer side 110. Like in other embodiments, the internal flow space 116 allows for the transportation of heat and/or fluid though the body portion 102 and relative to a skin surface of a residual limb. In an embodiment, air can flow into and out of the open proximal end of the membrane component 114 to help move and/or evaporate perspiration collected in the internal flow space 116 from the residual limb. In another embodiment, the membrane component 114 can be configured to absorb and/or wick perspiration or other fluid away from the residual limb and into the internal flow space 116 via the breathable region described below, and thereby reduce the opportunity for perspiration or other fluid to collect between the residual limb and the inner side of the body portion 102. The membrane component 114 is preferably a spacer structure but can comprise a foam material, a double layered textile, a thick textile, a 3-dimensional spacer, a technical knitting, combination thereof, or any other suitable member.

Figure 5A:
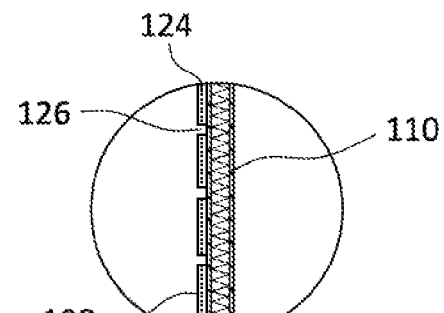
FIG. 5A is a detailed cross section of the prosthetic interface in FIG. 5.
Figure 5:
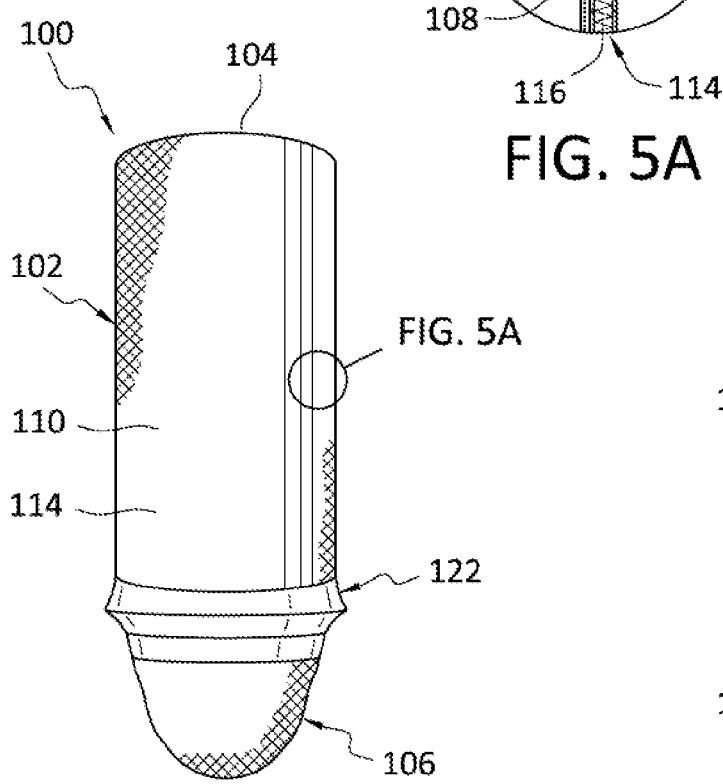
FIG. 5 is a side view of a prosthetic interface according to another embodiment.
Figure 6:
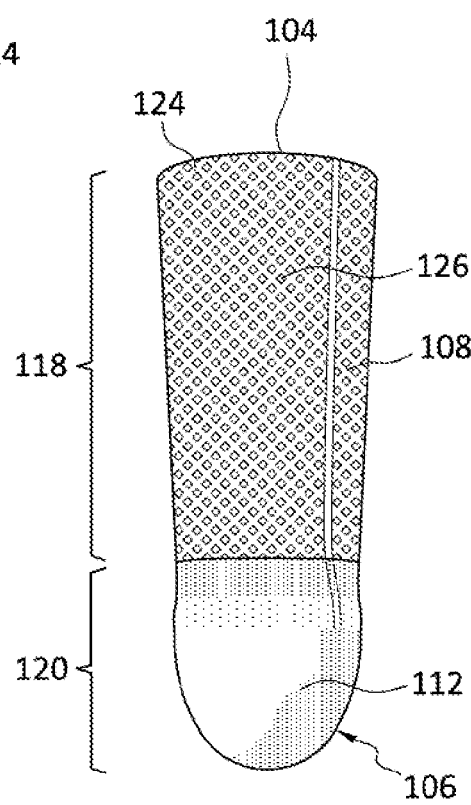
FIG. 6 is a side inverted view of the prosthetic interface in FIG. 5A.

Referring to FIGS. 5A and 6, at least one material coating 124 is applied to the inner side 108 that interacts with at least one of the membrane component 114 and the distal cup 112 to define at least one breathable region 118 along the inner side 108 that facilitates the removal of heat and fluid from the residual limb, and at least one impermeable region 120 that facilitates the formation of a seal between the prosthetic interface 100 and a prosthetic socket, permitting vacuum suspension of the prosthetic socket on the prosthetic interface 100. The prosthetic interface 100 thus provides both vacuum suspension and heat and perspiration management to a user.

In the illustrated embodiment, the at least one material coating 124 defines a plurality of voids 126 extending though the at least one material coating 124 along a length of the membrane component 114. The voids 126 are in fluid communication with the inner side 108 having a configuration permeable to fluid flow between the internal flow space 116 and the skin surface of the residual limb. The voids 126 can be through-holes or pin-holes in the at least one material coating 124. The voids 126 can be located along an entire length or a partial length of the membrane component 114. In the illustrated embodiment, the voids 126 extend along substantially an entire length of the membrane component 114.

The voids 126 may have consistent shapes and sizes throughout the at least one material coating 124, or may vary in shape, size, and pattern at different locations along the at least one material coating 124. For example, the voids 126 can be in distinct zones on the at least one material coating 124, anatomical patterns, or uniformly distributed on the at least one material coating 124. The voids 126 may define a variety of shapes such as round, oval, diamond, square, triangular, and other available shapes.

Proximal to the at least one impermeable region 120, the voids 126 in the at least one material coating 124 help define the at least one breathable region 118 of the membrane component 114 as they permit heat and moisture to flow between the skin surface of the residual limb and the internal flow space 116 of the membrane component 114.

Distal to the at least one breathable region 118, the voids 126 can interact with the distal cup 112 and the membrane component 114 to form the at least one impermeable region 120. For instance, the distal cup 112 can be formed of a polymeric material such as silicone and attached to the inner side 108 of the membrane component 114 at or near the distal end 106 as shown in FIG. 7. As the distal cup 112 is molded to the inner side 108 of the membrane component 114, a portion of the polymeric material forming the distal cup 112 can extend through the voids 126 in the at least one material coating 124 and into the internal flow space 116, thereby impregnating the membrane component 114 and securing the distal cup 112 to the membrane component 114. This mechanically and hermetically attaches the distal cup 112 to the membrane component 114.

The impregnated material also forms the at least one impermeable region 120 on the membrane component 114 because it physically creates a sealing bridge extending through the membrane component 114 and between the distal cup 112 and the outer side 110 of the membrane component 114. This sealing bridge allows an airtight seal to be created between the distal cup 112 and a seal component 122 attached to the membrane component 114, preventing a loss of vacuum due to movement of fluid through the internal flow space 116 between the distal end 106 and the at least one breathable region 118.

More particularly, the seal component 122 is attached to the outer side 110 of the membrane component 114 along the at least one impermeable region 120 so that pulling forces applied to the prosthetic interface 100 can result in the seal component 122 creating a suction between the prosthetic interface 100 and the prosthetic socket at the distal end 106 of the body portion 102, the suction tending to securely attach the prosthetic socket to the prosthetic interface 100. The seal component 122 can have any suitable configuration. For instance, the seal component 122 can include a first end attached to the body portion 102, and a second end arranged for deflection relative to the body portion 102.

The interaction of at least one material coating 124 with the membrane component 114 and the distal cup 112 can thus define a breathable interface on inner side 108 of the membrane component 114 for the removal of heat and/or fluid from a residual limb without compromising the ability of the prosthetic interface 100 to form a seal between the prosthetic interface 100 and a prosthetic socket for vacuum suspension.

The at least one material coating 124 can extend along an entire length or partial length of the membrane component 114. For instance, the at least one material coating 124 can terminate at or near a proximal end of the distal cup 112 such that the material forming the distal cup 112 seeps or bleeds through an exposed or permeable portion of the membrane component 114 distal to the at least one breathable region 118 omitting the at least one material coating 124. The distal cup 112 can be compression or injection molded to the membrane component 114.

Referring to FIG. 8, the prosthetic interface 100 may be constructed according to an embodiment between a male mold 128 and a female mold 130 of a molding system. The male mold 128 and the female mold 130 can be forced together with the female mold 130 engaging the outer side 110 of the membrane component 114 and a polymeric material such as silicone is positioned between the male mold 128 and the inner side 108 of the membrane component 114 to mold the distal cup 112 on the inner side 108 of the membrane component 114.

During compression molding of the distal cup 112, enough pressure can be exerted on the distal cup 112 to allow the silicone forming the distal cup 112 to penetrate the voids 126 of the at least one material coating 124 and fill the internal flow space 116 of the membrane component 114. According to an embodiment, the female mold 130 is heated such that the silicone forming the distal cup 112 cures before it can bleed through the outer side 110 of the membrane component 114 as the silicone forming the distal cup 112 bridges the distance between the seal component 122 and the inner side 108 of the membrane component 114. This beneficially allows for an airtight seal between the distal cup 112 and the seal component 122 when the seal component 122 is attached to the body portion 102. The filling of the internal flow space 116 with the silicone forming the distal cup 112 also advantageously prevents or reduces the likelihood of the membrane component 114 from collapsing when an elevated vacuum is applied to a distal region of a socket below the seal component 122. The distal cup 112 may also be formed through injection molding.

According to a variation, a recessed portion or rebate 132 can be created in the outer side 110 of the membrane component 114 during molding of the prosthetic interface 100. The rebate 132 can be sized and configured to facilitate attachment of the seal component 122 to the body portion 102. For instance, a base ring 134 of the seal component 122 carrying a deflectable sealing portion can be molded or adhered to the outer side 110 of the membrane component 114 such that the rebate 132 engages and limits distal movement of the seal component 122 during use, particularly as the seal component 122 engages a corresponding socket wall. In an embodiment, the seal component 122 can be molded in a same step as the distal cup 112. In other embodiments, the prosthetic interface 100 can be formed or molded without a rebate.

FIGS. 9 and 10 show a prosthetic interface 100A according to another embodiment including a membrane component 114A and a distal cup 112A. Referring to FIG. 9, at least one material coating 124A is applied to an inner side 108A of the membrane component 114A prior to molding the distal cup 112A to the inner side 108A of the membrane component 114A. The at least one material coating 124A is preferably silicone but can comprise any suitable material. In the illustrated embodiment, the at least one material coating 124A is configured not to bleed through the membrane component 114A. For instance, specific portions of the inner side 108A can be precoated with silicone to prevent or limit the at least one material coating 124A from bleeding into the internal flow space. In other embodiments, the at least one material coating 124A can be formulated not to bleed into the internal flow space.

The application of at least one material coating 124A is arranged to leave a permeable band 136 of the membrane component 114A exposed. The size of the permeable band 136 can be varied as desired. This can include remove the at least one material coating 124A from the inner side 108A to define the permeable band 136 or only applying the at least one material coating 124A on the inner side 108A beyond the permeable band 136.

Referring to FIG. 10, the at least one material coating 124A is configured to interact with the distal cup 112A and the membrane component 114A to form at least one impermeable region on the membrane component 114A like in other embodiments. More particularly, during molding of the distal cup 112A, the permeable band 136 allows a portion of a polymeric material 138 (e.g., silicone) forming the distal cup 112A to bleed or seep across the internal flow space. This seepage of the polymeric material 138 creates a sealing bridge between the distal cup 112A and the outer side 110A of the membrane component 114A, which, in turn, allows for the at least one impermeable region to be formed on the membrane component 114A, permitting for vacuum suspension between the prosthetic interface 100A and a prosthetic socket.

Optionally, a seal component can be adhered or otherwise attached to the membrane component 114A in the area of the permeable band 136, forming an airtight bond to the distal cup 112A on the inner side 108A of the prosthetic interface 100A. According to a variation, the internal flow space of the membrane component 114A distal to the permeable band can be substantially unfilled by the polymeric material 138 forming the distal cup 112A.

Figure 12:
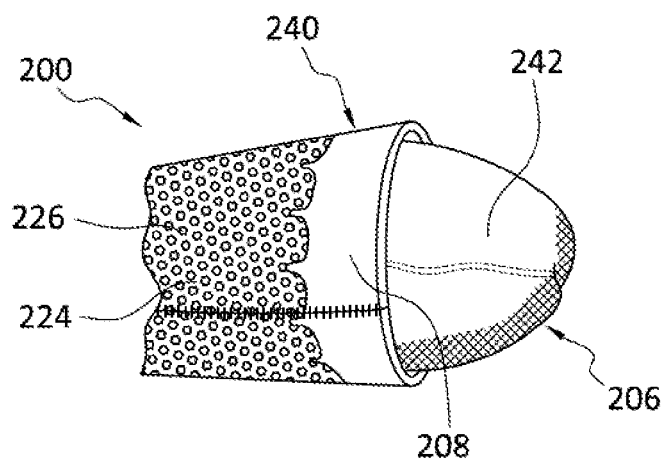
FIG. 12 a distal inverted view of the prosthetic interface in FIG. 11 without a distal cup for ease of reference.
Figure 11:
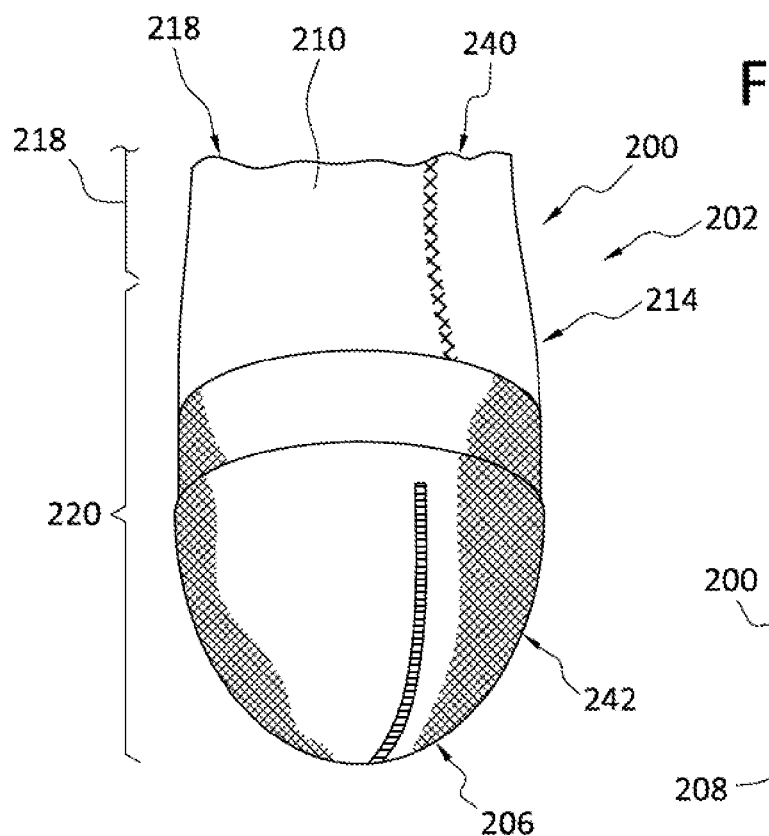
FIG. 11 is a perspective distal view of a prosthetic interface according to another embodiment.
Figure 13:
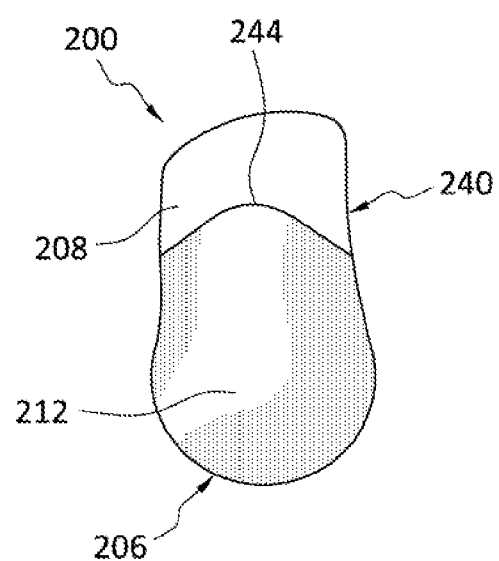
FIG. 13 is another distal inverted view of the prosthetic interface in FIG. 12 with the distal cup attached.

FIGS. 11-13 illustrates a prosthetic interface 200 according to yet another embodiment having a body portion 202 defining a proximal end, which is open, and a distal end 206, which is closed. Like other embodiments, the body portion 202 is formed at least in part by a membrane component 214 and a distal cup 212. The membrane component 214 has a flexible configuration defining an internal flow space extending along a length of the membrane component 214 between an inner side 208 arranged to face a skin surface of a residual limb and an outer side 210 arranged to face away from the skin surface. The internal flow space is capable of transporting heat and/or fluid through the membrane component 214 and relative to a skin surface of a residual limb. For instance, the internal flow space can be capable of transporting heat and perspiration generated by the residual limb through the membrane component 214 and away from the skin surface of the residual limb. The inner side 208 of the membrane component 214 is configured to be permeable to fluid, heat and moisture.

FIG. 12 shows the prosthetic interface 200 in an inverted position without a distal cup for ease of reference. In the illustrated embodiment, the membrane component 214 comprises a sleeve 240 comprising a spacer structure and a textile member 242 attached to a distal part of the sleeve 240. As described below, the combination of the sleeve 240 and the textile member 242 helps to facilitate discrete breathable and impermeable regions on the membrane component 214.

At least one material coating 224 is selectively applied to the inner side 208 of the sleeve 240 proximal to the textile member 242. The at least one material coating 224 preferably comprises a silicone material defines a plurality of pores 226 that allow air and moisture to pass through the at least one material coating 224 and into the internal flow space of the sleeve 240. This defines at least one breathable region 218 on the inner side 208 of the membrane component 214 that allows for fluid flow between the internal flow space and a skin surface of a residual limb. As seen in FIG. 12, the at least one material coating 224 can terminate proximally of the distal end of the sleeve 240. Further, the distal end of the at least one material coating 224 can define alternating coated and uncoated areas circumferentially around the sleeve 240, which, in turn, helps attach the distal cup 212 to the membrane component 214 and the at least one material coating 224.

To form at least one impermeable region 220 on the membrane component 214, a polymeric material forming the distal cup 212 is applied to an entire inner side of the textile member 242 and a distal part of the sleeve 240 distal to the at least one breathable region 218. The polymeric material extends through the textile member 242 and the distal part of the sleeve 240, mechanically and hermetically attaching the distal cup 212 to the membrane component 214.

Like in the previous embodiments, the polymeric material also forms a sealing bridge extending between the distal cup 212 and the outer side 210 of the membrane component 214 through the textile member 242, and optionally the distal part of the sleeve 240. This sealing bridge allows an airtight seal to be created between the distal cup 212 and a seal component. More particularly, a seal component can be attached or formed along the at least one impermeable region 220 to create an airtight seal with the distal cup 212 to allow for vacuum suspension between the prosthetic interface 200 and a prosthetic socket. The prosthetic interface 200 thus permits vacuum suspension of the prosthetic socket without loss of vacuum due to breathability in the at least one breathable region 218. The seal component can be a repositionable seal or a fixed seal. The textile member 242 can be configured to be thinner and more porous than the sleeve 240, which, in turn, facilitates impregnation of the polymeric material and provides an improved airtight interface for the seal component.

According to a variation, the distal cup 212 can be molded to the inner side 208 of the sleeve 240 such that a portion of the polymeric material forming the distal cup 212 extends over the top of at least one material coating 224 and through the pores 226, creating a mechanical attachment between the distal cup and the at least one material coating 224. In other embodiments, the distal end of the at least one material coating 224 can include cutouts or a jagged edge, which, can improve the attachment between the polymeric coating, the sleeve 240, and the at least one material coating 224.

FIG. 13 shows the prosthetic interface 200 in an inverted position with the distal cup attached 212 for ease of reference. As seen, the distal cup 212 completely covers the inner side of the textile member 242 and overlaps a length of the sleeve 240. The overlap between the distal cup 212 and the distal part of the sleeve 240 can help prevent the weight of the distal cup 212 from undesirably stretching or pulling on the textile member 242 as the sleeve 240 can support at least some of the weight of the distal cup 212. The amount of overlap between the distal cup 212 and the sleeve 240 can be controlled to vary the attachment strength between the distal cup 212 and the sleeve 240. For example, a longer overlap between the distal cup 212 and the sleeve 240 can increase the contact area between the sleeve 240 and the distal cup 212, which, in turn, can increase the attachment strength therebetween. The sleeve 240 underlying the distal cup 212 can be coated or uncoated by the at least one material coating 224.

According to a variation, the transition between the proximal end of the distal cup 212 and the sleeve 240 can define a wave finish or a varying thickness that decreases in a proximal direction toward a proximal edge 244 of the distal cup 212. This beneficially helps avoid a sharp transition or provides a more gradual transition between the distal cup 212 and the sleeve 240, increasing user comfort and reducing the likelihood of skin irritation along the proximal edge 244. The proximal edge 244 can also be rounded or curved along a wavy terminal edge, reducing the likelihood of skin irritation and/or pressure points from contact between the proximal edge 244 and the residual limb.

FIGS. 14-17 shows a prosthetic interface 300 according to yet another embodiment where the entire inner side of the prosthetic interface 300 can be breathable. The prosthetic interface 300 includes a body portion 302, defining a proximal end 304, which is open, and a distal end 306, which is closed. The body portion 302 is formed at least in part by a membrane component 314 and a distal cup 312. The membrane component 314 has a flexible configuration defining an internal flow space 316 extending along a length of the membrane component 314 between an inner side 308 arranged to face a skin surface of a residual limb and an outer side 310 arranged to face away from the skin surface. The internal flow space 316 is capable of transporting heat and/or fluid through the membrane component 314 and relative to the skin surface of the residual limb. The inner side 308 of the membrane component 314 configured to be permeable to heat and moisture.

At least one material coating is selectively applied to membrane component 314 to form at least one breathable region 318 on the inner side 308. The at least one material coating comprises a first material coating 324 applied to an entirety of the inner side 308 of the membrane component 314 and a second material coating 344 selectively applied to the outer side 310 of the membrane component 314. The first material coating 324 can be a silicone material covering the inner side 308.

Referring to FIG. 15, a plurality of voids 326 extend through the first material coating 324 and permit fluid flow between the internal flow space 316 and the skin surface of the residual limb. The voids 326 permit heat and/or fluid to flow from the residual limb into the internal flow space 316 of the membrane component 314 through the voids 326, helping to define the breathable region 318. The voids 326 may be distributed over the entire inner side 308 of the membrane component 314, making the entire inner side breathable, enhancing user comfort.

The voids 326 can comprise a plurality of strips formed in the first material coating 324 exposing the membrane component 314. The strips can extend obliquely along the inner side 308, across the inner side 308, can curve along the inner side 308, and/or can extend up and down along the inner side 308. In other embodiments, the strips can form anatomical patterns on the inner side 308. In other embodiments, the voids 326 may be provided in greater density in certain regions prone to increased heat and fluid buildup, e.g. in a popliteal region.

The second material coating 344 is applied to at least a distal region of the membrane component 314 along the outer side 310. The second material coating can include a polymeric material such as silicone and can help block or prevent the material forming the distal cup 312 from impregnating the internal flow space 316. For instance, the distal cup 312 can be molded in a sandwiched construction between the second material coating 344 on the outer side 310 of the membrane component 314 and a textile cover 346 arranged to reduce friction between the distal end 306 of the prosthetic interface 300 and a socket, facilitating donning and doffing of the socket. The distal cup 312 can be formed of a polymeric material such as silicone.

The location of the second material coating 344 between the internal flow space 316 and the distal cup 312 physically blocks the polymeric material forming the distal cup 312 from impregnating the internal flow space 316 at the distal end 306 radially inside of the distal cup 312, maintaining the at least one breathable region 318 along the inner side 308 of the membrane component 314 in the area of the distal cup 312.

The distal cup 312 thus forms an impermeable region 320 radially outside of the at least one breathable region 318 on the body portion 302. As such, the impermeable region 320 formed by the distal cup 312 overlaps the at least one breathable region 318 extending along the entire inner side 308 of the base. This beneficially allows for vacuum suspension via the impermeable region 320 and the entire residual limb to breathe within the prosthetic interface 300, improving user comfort and safety. For instance, an airtight seal can be created between the distal cup 312 and a seal component 322 attached to the outer side 310, allowing for vacuum suspension between the prosthetic interface 300 and a prosthetic socket.

According to a variation, a rebate 332 is formed on the distal cup 312 during molding of the prosthetic interface 300. The rebate 332 can be sized and configured to facilitate attachment of the seal component 322 to the body portion 302. In other embodiments, the distal cup 312 can be formed or molded without a rebate.

The prosthetic interface 300 may be constructed between a male mold 328 and a female mold 330 of a molding system as seen in FIG. 16. In an embodiment, the male and female molds 328, 330 can be forced together with the male mold 328 engaging the inner side 308 of the membrane component 314 and the silicone material and the textile cover 346 positioned between the female mold 330 and the outer side 310 of the membrane component 314 to compression mold the distal cup 312 on the outer side 310 of the membrane component 314. The textile cover 346 can be located between the silicone material and the female mold 330 such that the textile cover 346 covers the outer surface of the distal cup 312. The female mold 330 can be heated to stop or limit the silicone material forming the distal cup 312 from penetrating through the outer surface of the textile cover 346, for example by causing the silicone material proximate the textile cover 346 to cure before it can bleed entirely through the textile cover 346.

The rebate 332 can be created in the textile cover 346 or the distal cup 312 during molding of the prosthetic interface 300. For instance, a base ring 334 of the seal component 322 can be molded or adhered to textile cover 346 such that the rebate 332 engages and limits distal movement of the seal component 322 during use.

In other embodiments, the textile cover 346 can be omitted from the prosthetic interface 300. For instance, the distal cup 312 can be molded onto the outer side 310 of the membrane component 314 and a low-friction coating can be applied to the distal cup 312 to facilitate donning of a socket.

In an embodiment, the seal component 322 can be molded on the prosthetic interface 300 in a same step as the distal cup 312. In other embodiments, the seal component 322 can be attached to the textile cover 346 before forming the prosthetic interface 300 as shown in FIG. 17. For instance, the inner surface of the textile cover 346 may be coated or may not be coated to form an airtight attachment with the seal component 322 before compression molding the prosthetic interface 300.

FIG. 18-20 illustrate a prosthetic interface 400 according to yet another embodiment that provides the option of using adjustable seal components or fixed seal components. The prosthetic interface 400 includes a body portion 402 formed at least in part by a membrane component 414 having a proximal end 404, which is open, and a distal end 406, which is closed. The membrane component 414 has a flexible configuration defining an internal flow space 416 extending along a length of the membrane component 414 between an inner side 408 arranged to face a skin surface of a residual limb and an outer side 410 arranged to face away from the skin surface.

Like in other embodiments, at least one material coating 424 is selectively applied to the membrane component 414 to form at least one breathable region 418 on an inner side 408 and at least one impermeable region 420 capable of carrying at least one seal component. In the illustrated embodiment, the seal component 422 is secured to an outer surface 402A of the body portion 402 among at least one seal band 450 formed along the outer surface 402A. The at least one seal band 450 can comprise a plurality of seal bands formed of a frictional material to maintain the seal component 422 on the prosthetic interface 400. The seal component 422 frictionally fits against at least one of the seal bands 450 and can be movably positioned along the impermeable region 420 forming an airtight bond between the body portion 402 and the seal component 422. In other embodiments, the seal component 422 can be adhered to the body portion 402 among different seal bands 450 within the impermeable region 420. The prosthetic interface 400 thus beneficially provides the option of using adjustable seal components or fixed seal components. In yet other embodiments, the seal component 422 can be positioned among different seal bands 450 within the breathable region 418 when lower suspension levels are needed, such as during lighter activity periods or when laying down.

As shown best in FIG. 18B, the membrane component 414 is positioned inside of the prosthetic interface 400. The membrane component 414 is preferably a spacer structure but can comprise a foam material, a double-layered textile, a thick textile, a 3-dimensional spacer, a technical knitting, combination thereof, or any other suitable member.

Referring to FIG. 18B, the body portion 402 includes an elastomeric body portion having a wall portion 456 and the membrane component 414 positioned radially inside of the wall portion 456. In an embodiment, the seal bands 450 protrude from an outer surface 402A of the body portion 402. The seal bands 450 define a variety of shapes such as bubble, dome, arcuate, square, and other available shapes that may be molded over the body portion 402. The seal bands 450 are desirably arranged to bleed through a textile cover 454 forming the outer surface of the body portion 402 such that a portion of the seal bands 450 is located in the textile cover 454. The seal bands 450 extend through the textile cover 454 to the wall portion 456 formed of a polymeric material adjacent to the outer side 410 of the membrane component 414. The wall portion 456 can be molded or otherwise attached to the outer side 410 of the membrane component 414 or to a material coating applied to the outer side 410 as described below. The wall portion 456 can define an open proximal end and a closed distal end. The polymeric material forming the wall portion 456 can also form the distal cup 412.

In the illustrated embodiment, the at least one material coating 424 comprises a first material coating 424 applied to the outer side 410 of the membrane component 414 facing away from the skin surface of the residual limb. The length including the first material coating 424 thus separates the wall portion 456 from the membrane component 414. The first material coating 424 can include a polymeric material such as silicone configured and positioned to stop the polymeric material forming the wall portion 456 from impregnating the internal flow space 416 of the membrane component 414 during formation or molding of wall portion 456, maintaining the internal flow space 416 along the length of the membrane component 414 corresponding to the first material coating 424.

A second material coating can be applied to the inner side 408 of the membrane component 414 to enhance gripping or attachment at the interface between the residual limb and the prosthetic interface 400. The second material coating can include a plurality of voids to help heat and fluid to flow from the skin surface of the residual limb into the internal flow space 416 of the membrane component 414 along the breathable region 418 and to be transported via the channels defined therein. In an embodiment, the second material coating can extend along an entire length of the membrane component 414.

The first material coating 424 along the outer side 410 of the membrane component 414 can be controlled to vary the bleed or seepage of the polymeric material forming the wall portion 456 through the membrane component 414 which, in turn, can help create the impermeable region 420 and hence an airtight interface between the prosthetic interface 400 and the seal component 422. For instance, the first material coating 424 can extend from the proximal end 404 of the body portion 402 to a bleed through line A such that the membrane component 414 distal to the point A is exposed by the first material coating 424 or permeable to polymeric material. As discussed below, this exposed region may generally correspond to the distal cup 412 formed by the wall portion 456.

During molding of the wall portion 456 on the body portion 402, sufficient pressure can be applied to the polymeric material forming the wall portion 456 (including the distal cup 412) such that it seeps or penetrates through the exposed region of the membrane component 414 below a bleed through line A and fills the internal flow space 416 of the membrane component 414. In an embodiment, the polymeric material forming the wall portion 456 can be arranged to cure before it bleeds through the inner side 408 of the membrane component 414 as the polymeric material bridges the distance between wall portion 456 and the inner side 408 of the membrane component 414. This beneficially attaches the wall portion 456 to the membrane component 414 and helps create an airtight interface between the wall portion 456 and the inner side 408 of the membrane component 414 in the impermeable region 420. The filling of the internal flow space 416 with the polymeric material forming the wall portion 456 also advantageously prevents or reduces the likelihood of the membrane component 414 collapsing under a compressive load.

Within the impermeable region 420 along the length of the body portion 402, the seal component 422 can frictionally fit and seal against at least one of the seal bands 450 and has the flexibility to be installed among different seal bands 450 because the thickness of the body portion 402 is airtight between the inner side 408 of the membrane component 414 and the seal bands 450. More particularly, the seal component 422 can create an airtight seal between the seal component 422 and the impermeable region 420 to allow for vacuum suspension between the prosthetic interface 400 and a socket. The seal component 422 can likewise be removed from the body portion 402 and readjusted as considered necessary at a new location. The prosthetic interface 400 thus beneficially is breathable and provides the option of using adjustable seal components rather than fixed seal components without compromising the effectiveness of the vacuum seal.

In an embodiment, the length or area of the impermeable region 420 along the longitudinal axis of the body portion 402 can be increased to provide a greater area on the body portion 402 over which the seal component 422 can be attached. In other embodiments, the length or area of the breathable region 418 along the longitudinal axis of the body portion 402 can be increased or provide larger breathable interface between the residual limb and the body portion 402.

According to an embodiment, the distal end 406 of the body portion 402 can include an attachment pin arranged to extend through a pin bore formed in the distal end of a socket, allowing for a mechanical lock in addition to the vacuum lock between the prosthetic interface 400 and the socket.

In an embodiment, a proximal edge of the membrane component of the present disclosure can be open to atmosphere and in fluid communication with the internal flow space of the membrane component as described above. This beneficially facilitates the transportation of fluid and heat out of the membrane component via the proximal edge.

According to a variation, the membrane component includes an edge finishing part configured to close or cover the proximal edge of the prosthetic interface. The edge finishing part can extend around all or a portion of a circumference of the prosthetic interface. This beneficially can reduce the likelihood of skin irritation from the proximal edge and/or facilitate custom fitting of the prosthetic interface on a residual limb. It also can help limit migration of the membrane component and/or prevent undesirable slipping between the membrane component and the residual limb.

Figure 21:
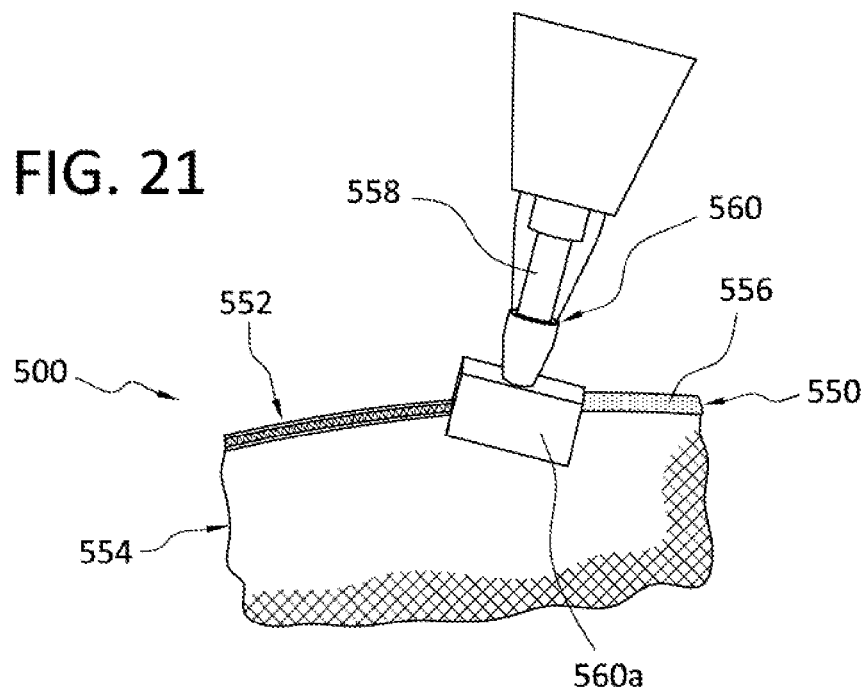
FIG. 21 is a side view of a prosthetic interface according to another embodiment.

Referring to FIG. 21, an edge finishing part 550 is shown at least in part closing and/or covering a proximal edge 552 of a membrane component forming part of a prosthetic interface 500. The edge finishing part 550 can comprise a material 556 such as silicone or other suitable material applied to the proximal edge 552 via a mixer 558 and an extruder 560. The edge finishing part 550 can extend around all or a portion of circumference of the prosthetic interface 500. In an embodiment, the edge finishing part 550 can have an impermeable configuration such that the edge finishing part 550 seals the proximal edge 552. In other embodiments, the edge finishing part 550 can have a permeable configuration such that air and/or heat can move through the proximal edge 552 via the edge finishing part 550. For instance, the edge finishing part 550 can include a plurality of perforations in communication with the gap and/or passageways of the breathable membrane component as described above.

The extruder 560 can define a port in communication with the material 556 inside of the mixer 558, and an applicator 560a. The applicator 560a is configured to fit over the proximal edge 552 and form the edge finishing part 550 on the proximal edge 552 as the material 556 exits the port and the applicator 560a is moved along the proximal edge 552. In an embodiment, the material 556 can be applied to the proximal edge 552 via the mixer 558 and the extruder 560 after the breathable membrane component 554 has been cut to fit a length of the residual limb. This beneficially allows a user or clinician to easily form and attach the edge finishing part 550 to the proximal edge 552 after the prosthetic interface 500 has been formed and/or cut to fit.

Figure 22:
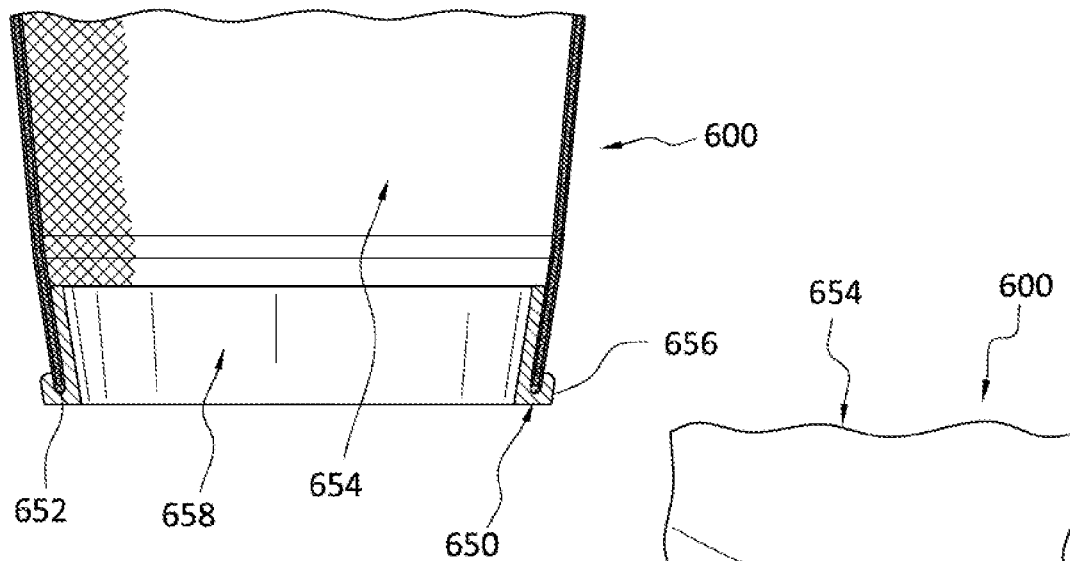
FIG. 22 is a schematic cross section of a mold assembly for molding a prosthetic interface according to another embodiment.
Figure 23:
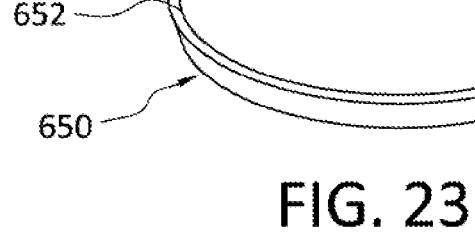
FIG. 23 is a side view of the prosthetic interface in FIG. 22.

According to another embodiment, an edge finishing part 650 can comprise an overmold portion 656 as shown in FIGS. 22 and 23. A proximal edge 652 of the membrane component 654 can be pressed in a mold 658 configured to mold the overmold portion 656 on the proximal edge 652 to form the edge finishing part 650. The overmold portion 656 can include a softer or different material than the membrane component 654. The overmold portion 656 can comprise silicone or another elastomeric material. The overmold portion 656 can extend around all or a portion of a circumference of the prosthetic interface 600. Like the previous embodiment, the overmold portion 656 can be attached to the proximal edge 652 after the prosthetic interface 600 has been formed and/or cut to fit. The overmold portion 656 also can have a permeable or impermeable configuration and can help reduce the likelihood of skin irritation and/or slippage between the breathable membrane component and the residual limb.

According to yet another variation, an edge finishing part comprises a shaped member that is preformed (e.g., pre-molded or extruded) and then attached or fixed to a proximal edge of a membrane component forming at least part of prosthetic interface. Like the previous embodiment, the edge finishing part can be attached to the proximal edge after the prosthetic liner has been formed and/or cut to fit. It also can have a permeable or impermeable configuration and can help reduce the likelihood of skin irritation and/or slippage between the breathable membrane component and the residual limb. The shaped member can include a silicone coated fabric or woven material. The shaped member can include synthetic fibers.

Figure 24:
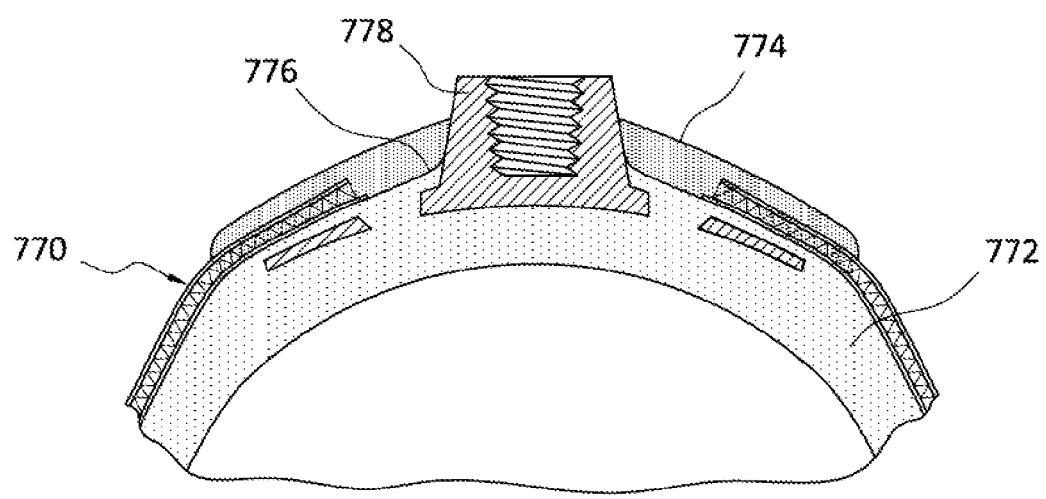
FIG. 24 is distal cross section view of a prosthetic interface according to another embodiment.

FIG. 24 shows a prosthetic interface according to yet another embodiment comprising a prosthetic sock including a body portion. The body portion is formed at least in party by a membrane component 770 and a distal cup 772 formed of a silicone or other polymeric material. A cap portion 774 formed of an elastomeric material (e.g., silicone) is molded onto the outside of the distal end of the membrane component 770. The cap portion 774 defines an opening 776 for receiving a threaded connector 778 that enables interconnection between the membrane component 770 and a prosthetic device (e.g., a socket or a lock assembly). According to a variation of manufacturing the prosthetic interface, the threaded connector 778 can be positioned in the opening 776 before the distal cup 772 is molded on the inner side of the membrane component 770 such that the threaded connector 778 is secured between the distal cup 772 and the cap portion 774. The various aspects and embodiments disclosed herein are for purposes of illustration and are not intended to be limiting. For instance, the membrane component can improve cushioning and/or volume compensation of the prosthetic interface. In an embodiment, the membrane component comprises a spacer structure with the first layer and/or the second layer being flexible and the supporting elements can comprise nanofibers that are resiliently deformable such that they can sway and/or bend relative to one another between the first and second layers. When the spacer structure is loaded, the first layer, for example, can flex under the load and the supporting elements can deform between the first and second layers to extract energy from the movement between the first and second layers, which, in turn, provides an amount of cushioning and protection to the residual limb. The spacer structure can thus reduce force exerted on and/or within the prosthetic interface, making it more suitable for prolonged use and/or higher levels of activity.

The spacer structure of the present disclosure may be arranged to help accommodate volume changes of the residual limb. For instance, the spacer structure can be resiliently compressed between the residual limb and a prosthetic socket when the prosthetic interface is donned. As the residual limb loses volume, stored energy in the supporting elements can force the first and second layers apart to expand the spacer structure and consequently the prosthetic interface in the radial or circumferential direction, compensating for the loss of volume. As the residual limb increases in volume, the spacer structure can resiliently compress between the residual limb and the prosthetic socket, storing energy and accommodating the increased size of the residual limb.

In an embodiment, the spacer structure of the present disclosure can be arranged to move fluid and heat relative to the residual limb. In an embodiment, when the spacer structure is loaded, at the first layer and supporting elements are deformed such that the first and second layers move toward one another, reducing a volume of the breathable space. This decrease in volume of the breathable space expels fluid and heat in the breathable space out of the spacer structure. When the load is removed from the spacer structure, the spacer structure returns to its original or resting position. The inherent properties of the material of the first and second layers, and/or the supporting elements can help return the spacer structure to its original or resting position. During the return of the spacer structure to its resting position, air can be pulled or drawn into the breathable space, which, in turn, ventilates the breathable spacer, advantageously helping to remove heat and additional fluid from the residual limb.

In other embodiments, the supporting elements can be varied to perform a specific performance or function of the spacer structure. For instance, the supporting elements can be arranged to have a greater density such that the spacer structure has a higher compressive stiffness. In other embodiments, diameters of the supporting elements can be varied to control the compressive stiffness of the spacer structure. In other embodiments, alignment of the supporting elements can be varied to control the amount of stiffness in the spacer structure. In other embodiments, alignment of the supporting elements can be adjusted in discrete areas to create regions having different properties in the spacer structure. In yet other embodiments, the size (e.g., length, width, and/or diameter) of the supporting element can be varied to control cushioning in specific areas of the prosthetic interface. In other embodiments, one or more of the supporting elements can have a hollow configuration to control the amount of stiffness and/or permeability of the spacer structure. All of these variations may advantageously provide regions and/or patterns of cushioning, rigidity, or other properties as needed for specific applications or regions.

As discussed above, it will be appreciated that embodiments of the membrane component can be configured to facilitate movement of fluid toward and/or away from the skin surface through membrane component. For instance, the membrane component can be configured to deliver a cooling fluid, an ointment, antiperspirant, an antibacterial agent, Aloe vera, combinations thereof, or any other suitable fluid or medicament to the skin surface via the internal flow space of the membrane component. In other embodiments, the prosthetic interface can be operatively coupled to a pump system that supplies cooler air to the skin surface through the internal flow space of the membrane component, reducing the buildup of heat within the prosthetic interface. As such, the membrane component can help manage the buildup of heat and sweat within the prosthetic interface by introducing and/or removing fluid from the skin surface of a residual limb.

The prosthetic interface embodiments of the present disclosure advantageously overcome limitations of existing prosthetic interfaces by providing a prosthetic interface that combines breathability to mitigate buildup of fluid and heat without compromising the ability of the prosthetic interface to form a reliable vacuum suspension between the prosthetic interface and a corresponding prosthetic socket. The arrangement of a membrane component defining an internal flow space and at least one material coating selectively applied to the membrane component to form at least one breathable region on an inner side of the membrane component and at least one impermeable region associated with the outer side of the membrane component advantageously seals a portion of the prosthetic interface from atmospheric pressure while allowing breathability in another part. Additionally, the membrane component in combination with the at least one material coating can provide additional beneficial features such as interfacing features, additional cushioning, etc.

It is to be understood that not necessarily all objects or advantages may be achieved under any embodiment of the disclosure. Those skilled in the art will recognize that the suspension liner may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct a prosthetic interface in accordance with principles of the present disclosure.

Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A prosthetic interface comprising:
   a body portion including a proximal end having an open configuration, and a distal end having a closed configuration, the body portion formed by a membrane component having a flexible configuration defining an internal flow space extending along a length of the membrane component between an inner side arranged to face a skin surface of a residual limb and an outer side arranged to face away from the skin surface, the internal flow space arranged to transport fluid through the membrane component and relative to the skin surface; and
   a distal cup formed of a polymeric material at the distal end of the body portion;
   at least one material coating selectively applied to the membrane component such that the at least one material coating interacts with at least one of the membrane component and the distal cup to define a breathable region, and an impermeable region along the outer side that allows for vacuum suspension between the prosthetic interface and a prosthetic socket;
   wherein the body portion includes an elastomeric wall portion and the membrane component is positioned radially inside of the wall portion along an inner side of the elastomeric wall portion.

2. The prosthetic interface of claim 1, wherein the membrane component defines an inner side and an outer side, the at least one material coating extending along the outer side of the membrane component.

3. The prosthetic interface of claim 1, wherein the at least one material coating is formed from an elastomeric material.

4. The prosthetic interface of claim 3, wherein the at least one material coating prevents the elastomeric wall portion from impregnating the membrane component.

5. The prosthetic interface of claim 4, wherein the internal flow space of the membrane component is maintained along an axial length thereof.

6. The prosthetic interface of claim 1, wherein a textile cover extends along an outer side of the elastomeric wall portion.

7. The prosthetic interface of claim 6, wherein at least one seal band protrudes from an outer side of the textile cover and bleeds through the textile cover to engage the elastomeric wall portion.

8. The prosthetic interface of claim 7, wherein the at least one seal band is formed from a polymeric material.

9. The prosthetic interface of claim 1, wherein the membrane component defines an inner side and an outer side;
   wherein the at least one material coating includes a first material coating located on an outer side of the membrane component, and a second material coating located on an inner side of the membrane component.

10. The prosthetic interface of claim 9, wherein the second material coating defines a plurality of voids permitting fluid to flow from the skin surface into the internal flow space of the membrane component.

11. The prosthetic interface of claim 10, wherein the second material coating extends along an entirety of the inner side of the membrane component.

12. The prosthetic interface of claim 9, wherein the first material coating forms an impermeable barrier to the outer side of the membrane component.

13. The prosthetic interface of claim 9, wherein the first material coating extends from the proximal end of the body portion to a bleed-through line such that the membrane component distal at a predetermined point along the bleed-through line is exposed by the first material coating, said predetermined point demarcating the breathable region, and the impermeable region.

14. The prosthetic interface of claim 13, wherein the elastomeric wall portion extends along an outer side of the first material coating, and penetrates the membrane component by extending through an exposed region of the first material coating in the impermeable region to fill the internal flow space.

15. The prosthetic interface of claim 1, wherein within the impermeable region along the length of the body portion, a seal component is arranged to selectively frictionally fit and seal against at least one seal band integrated with the body portion.

16. The prosthetic interface of claim 15, wherein the at least one seal band defines at least two seal bands, such that a thickness of the body portion is airtight between the inner side of the membrane component and the seal bands.

17. The prosthetic interface of claim 1, wherein a length or area of the impermeable region along the longitudinal axis of the body portion is less than the breathable region.

18. A prosthetic interface comprising:
   a body portion including a proximal end having an open configuration, and a distal end having a closed configuration, the body portion formed by a membrane component having a flexible configuration defining an internal flow space extending along a length of the membrane component between an inner side arranged to face a skin surface of a residual limb and an outer side arranged to face away from the skin surface, the internal flow space arranged to transport fluid through the membrane component and relative to the skin surface, the body portion including an elastomeric wall portion and the membrane component is positioned radially inside of the wall portion along an inner side of the elastomeric wall portion; and
   a textile cover extends along an outer side of the elastomeric wall portion;
   a distal cup formed of a polymeric material at the distal end of the body portion;
   at least one material coating selectively applied to the membrane component such that the at least one material coating interacts with at least one of the membrane component and the distal cup to define a breathable region, and an impermeable region along the outer side that allows for vacuum suspension between the prosthetic interface and a prosthetic socket;
   wherein the membrane component defines an inner side and an outer side, the at least one material coating extending along the outer side of the membrane component;
   wherein the at least one material coating is formed from an elastomeric material.

19. A prosthetic interface comprising:

a body portion including a proximal end having an open configuration, and a distal end having a closed configuration, the body portion formed by a membrane component having a flexible configuration defining an internal flow space extending along a length of the membrane component between an inner side arranged to face a skin surface of a residual limb and an outer side arranged to face away from the skin surface, the internal flow space arranged to transport fluid through the membrane component and relative to the skin surface, the body portion including the elastomeric wall portion and the membrane component is positioned radially inside of the wall portion along the inner side of the elastomeric wall portion;

a distal cup formed of a polymeric material at the distal end of the body portion;

at least one material coating selectively applied to the membrane component such that the at least one material coating interacts with at least one of the membrane component and the distal cup to define a breathable region, and an impermeable region along the outer side that allows for vacuum suspension between the prosthetic interface and a prosthetic socket;

wherein the membrane component defines an inner side and an outer side, the at least one material coating including a first material coating located on an outer side of the membrane component, and a second material coating located on an inner side of the membrane component.

* * * * *